United States Patent [19]

Klauke et al.

[11] 4,439,620

[45] Mar. 27, 1984

[54] 2,4-DICHLORO-5-FLUOROBENZOYL HALIDE AND A PROCESS FOR ITS PREPARATION

[75] Inventors: Erich Klauke; Klaus Grohe, both of Odenthal, Fed. Rep. of Germany

[73] Assignee: Bayer Aktiengesellschaft, Leverkusen, Fed. Rep. of Germany

[21] Appl. No.: 397,958

[22] Filed: Jul. 14, 1982

[30] Foreign Application Priority Data

Oct. 29, 1981 [DE] Fed. Rep. of Germany ....... 3142856

[51] Int. Cl.³ .............................................. C07C 63/04
[52] U.S. Cl. .................................... 562/493; 544/362; 544/363; 546/156; 260/544 D; 560/47; 568/425; 568/437; 570/127
[58] Field of Search .................. 562/493; 260/544 D; 568/437; 470/127

[56] References Cited

U.S. PATENT DOCUMENTS

3,156,553  11/1964  Searle ............................ 260/544 D

FOREIGN PATENT DOCUMENTS

2840924  12/1979  Fed. Rep. of Germany ... 260/544 D

*Primary Examiner*—Paul J. Killos
*Attorney, Agent, or Firm*—Sprung, Horn, Kramer & Woods

[57] ABSTRACT

The invention relates to 2,4-dichloro-r-fluorobenzoyl halide (particularly the chloride) and methods for its production. Also included in the invention are intermediates useful for the production of said 2,4-dichloro-5-fluorobenzoyl halide (particularly the chloride).

16 Claims, No Drawings

2,4-DICHLORO-5-FLUOROBENZOYL HALIDE AND A PROCESS FOR ITS PREPARATION

The present invention relates to the new compounds 2,4-dichloro-5-fluorobenzoyl halide (particularly chloride), which is a valuable intermediate produce in the synthesis of highly active antibacterial medicaments, to a process for its production and to certain novel intermediate compound used in that process.

2,4-Dichloro-5-fluorobenzoyl halide (particularly chloride) has not hitherto been described. However, it is required as an intermediate product in the synthesis of antibacterially highly active 1-cyclopropyl-6-fluoro-1,4-dihydro-4-oxo-7-piperazino-quinoline-3-carboxylic acids, which are the subject of our copending application corresponding to German Patent Application P No. 31 42 854.1, filed on the Oct. 29, 1981.

According to the present invention there is provided, as a new compound, 2,4-dichloro-5-fluorobenzoyl halide (particularly chloride) of the formula

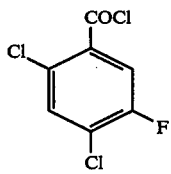

(I)

The present invention further provides a process for the production of 2,4-dichloro-5-fluorobenzoyl halides of formula (I), in which, for example, (a) 2,4-dichloro-5-fluoro-1-trichloromethylbenzene of the formula

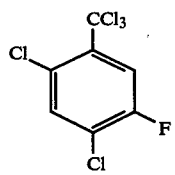

(IV)

is reacted with sulphuric acid to give 2,4-dichloro-5-fluorobenzoic acid of the formula

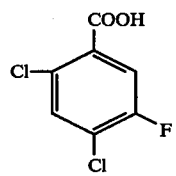

(VI)

which is then reacted with thionyl chloride to give the compound of formula (I), or (b) 2,4-dichloro-5-fluoro-1-trichloromethylbenzene of formula (IV) is reacted with water in the presence of a catalyst, or (c) 2,4-dichloro-5-fluorobenzal chloride of the formula

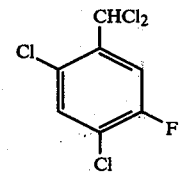

(V)

is converted with sulphuric acid into 2,4-dichloro-5-fluorobenzaldehyde of the formula

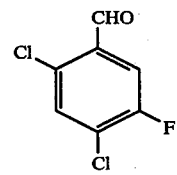

(VII)

which is then chlorinated to give the compound of formula (I).

In carrying out reaction variants (a) and (c), the sulphuric acid used is generally approximately 95% strength by weight sulphuric acid.

In general, reaction variant (b), is carried out by partially hydrolysing the compound of formula (IV) with a calculated amount of water in the presence of $FeCl_3$ as a catalyst.

Preferably the compound of formula (IV), or the compound of formula (V), used as a starting material in reaction variants (a), (b) and (c), respectively has been obtained by diazotising 3-amino-4,6-dichlorotoluene of the formula

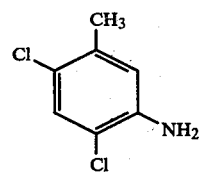

(II)

coupling with dimethylamine, reacting the product with hydrofluoric acid and thermally cleaving the fluorinated product to give 3-fluoro-4,6-dichlorotoluene of the formula

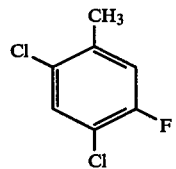

(III)

chlorinating the compound of formula (III) and separating off the desired product of formula (IV) or (V).

In detail, the preparation of the compound of formula (IV) or the compound of formula (V) is generally carried out as follows:

2,4-Dichloro-5-fluorobenzoyl chloride of formula (I) is prepared by diazotising 3-amino-4,6-dichlorotoluene of formula (II), coupling the diazo solution with dimethylamine to the corresponding triazene, which, in excess, anhydrous hydrofluoric acid, is initially converted into 2,4-dichloro-5-methyldiazonium fluoride and then without intermediate isolation by thermal cleavage at 130° to 140° C. into 3-fluoro-4,6-dichlorotoluene of formula (III). (The compound of formula (III) can also be obtained by thermally cleaving 2,4-dichloro-5-methyldiazonium tetrafluoroborate at a temperature of 160° to 170° C.). Chlorination of the compound of formula (III) at 110° to 160° C. under UV irradiation produces a mixture which can be separated by distillation into its components 2,4-dichloro-5-fluoro-1-trichloromethylbenzene of formula (IV) and 2,4-dichloro-5-fluorobenzal chloride of formula (V).

The bromides and fluorides corresponding to the compound of formula (I) can be prepared as follows:

If the compound of formula (VI) is treated with phosphorus tribromide instead of with thionyl chloride, 2,4-dichloro-5-fluorobenzoyl bromide (VIII) is obtained.

2,4-Dichloro-5-fluorobenzoyl fluoride (IX) can be prepared from the compound of formula (I) by reaction with hydrofluoric acid.

The reaction variants according to the present invention and processes for the production of bromides and fluorides corresponding to the compound of formula (I), as well as a process for the production of the starting materials are shown in the reaction scheme below.

formula (VIII) and fluoride of formula (IX), can be converted into highly active, antibacterial medicaments. (This conversion is the subject of our previously mentioned German copending application P No. 31 42 954.1 of the same date as the present application).

This conversion may be carried out, for example, as follows:

The compound of formula (I), (VIII) or (IX) is reacted with β-cyclopropylaminoacrylic acid methyl ester of formula (X) to produce, via an acylated intermediate product of formula (XI) (melting point 149° to 150° C.), the ester of formula (XII) (melting point 226° to 228° C.) which is subjected to alkaline hydrolysis to give 7-chloro-1-cyclopropyl-6-fluoro-1,4-dihydro-4-oxoquinoline-3-carboxylic acid of formula (XIII) (melting point 238° to 240° C.). The reaction of the latter compound with piperazine produces 1-cyclo-propyl-6-fluoro-1,4-dihydro-4-oxo-7-piperazinoquinoline-3-carboxylic acid of formula (XIV) (decomposition point 255° to 257° C.). This compound of formula (XIV) is distinguished by excellent activity against gram-positive and gram-negative bacteria and it exceeds in this respect by the compound known from DE-OS (German Published Specification) No. 2,804,097 equivalent to U.S.

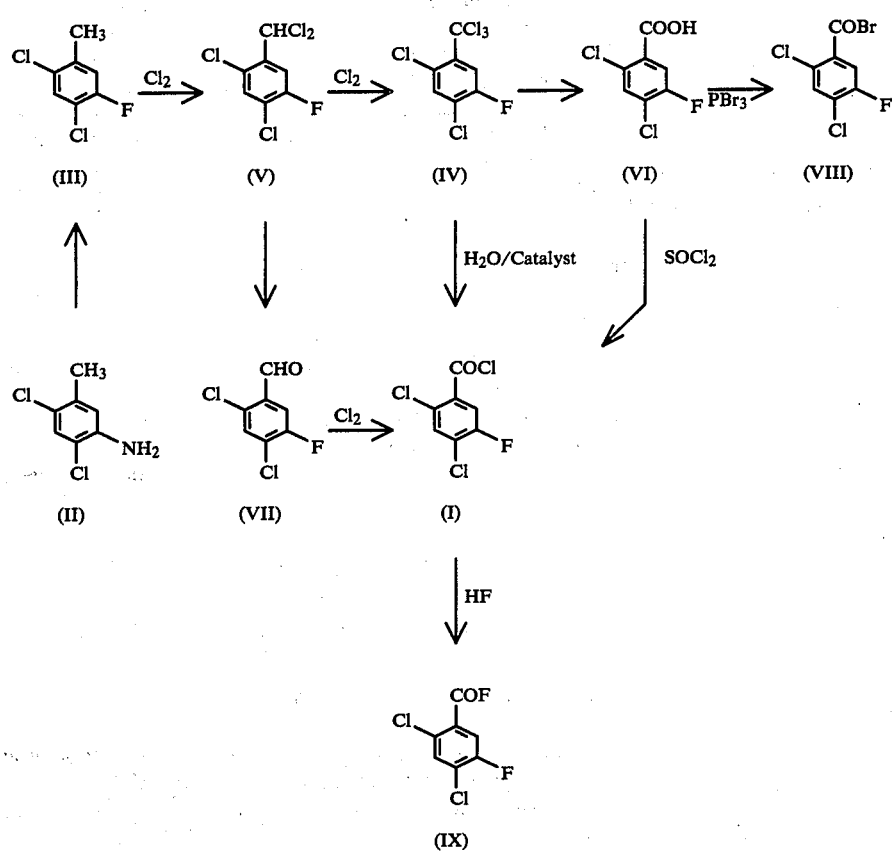

The starting compounds of formulae (III), (IV), (V), (VI) and (VII) are also novel and form a further subject of the present invention.

The compound of formula (I) according to the present invention, as well as the corresponding bromide of Pat. No. 4,146,719.

The conversion of compound of formula (I) according to the invention into the compound of formula (XIV) is shown in the reaction scheme below.

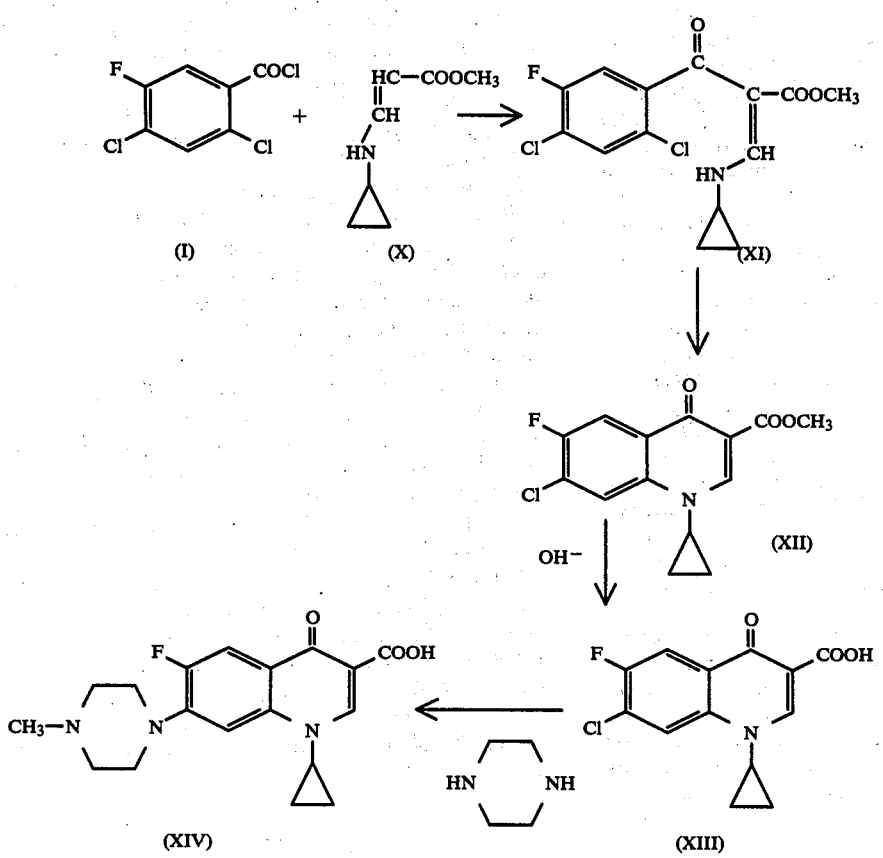

The following Examples 1 to 3 illustrate processes for the production of the compound of formula (I) of the present invention, whilst Example 4 illustrates the production of starting materials.

EXAMPLE 1

(Reaction variant (a))

730 g of 95% strength $H_2SO_4$ were initially introduced, and 323 g of 2,4-dichloro-5-fluoro-1-trichloromethylbenzene of formula (IV) were added dropwise with vigorous stirring at 40° C. The reaction was slightly exothermic; the rate at which the dropwise addition was carried out was so adjusted that the evolution of gas was brisk. After the dropwise addition was complete further stirring was continued until the evolution of gas was complete. The batch was discharged onto ice, and the resulting crystals were filtered off with suction and washed thoroughly with $H_2O$. Careful drying produced 232 g of 2,4-dichloro-5-fluorobenzoic acid of formula (VI) having a melting point of 141° to 142° C. The yields were between 97% and 98%.

This compound can also be prepared by replacing the amino group in 2,4-dichloro-5-aminobenzoic acid with fluorine by one of the known methods for this purpose, for example by a Balz-Schiemann reaction.

182 g of 2,4-dichloro-5-fluorobenzoic acid of formula (VI) and 250 ml of thionyl chloride together were initially introduced (the molar ratio of acid: $SOCl_2$ being 1:4). The mixture was heated with caution and at a rate appropriate to the resulting evolution of gas to 88° C. and further stirred at this temperature until the evolution of gas was complete. Excess $SOCl_2$ was distilled off under atmospheric pressure via a bridge, and the residue was fractionated by a column. After a small amount of first runnings of about 2 to 3 g, 2,4-dichloro-5-fluorobenzoic acid chloride of formula (I) distilled over at a boiling point of 121°/20 mbar. The refractive index was $n_D^{20}$: 1.5722. The yields were between 83% and 89% of theory.

If the compound of formula (VI) was treated with phosphorus tribromide instead of with thionyl chloride 2,4-dichloro-5-fluorobenzoyl bromide of formula (VIII), boiling point 134°/21 mbar and $n_D^{20}$: 1.5991, was obtained.

EXAMPLE 2

(Reaction variant (b))

565 g ( 2 mol) of 2,4-dichloro-5-fluoro-1-trichloromethylbenzene of formula (IV) were initially introduced and heated to 125° to 130° C. After the addition of a trace of $FeCl_3$ (fresh material), 36 g of water were slowly added dropwise at this temperature. Brisk evolution of gas immediately commenced. At the start of the reaction the rate for the dropwise addition was kept very low, whilst when the evolution of off-gas became brisk the rate at which the dropwise addition was carried out could be increased. The reaction took about 4 hours. Further stirring was continued until no further evolution of gas was observed, and the mixture was cooled down, filtered and distilled. The acid chloride of formula (I) boiled without first runnings, at boiling point 121°/20 mbar and it had a refractive index of $n_D^{20}$: 1.5722. The yields were between 85% and 93% of theory.

EXAMPLE 3

(Reaction variant (c))

687 g of 95% strength H₂SO₄ were initially introduced, and 266 g of 2,4-dichloro-5-fluorobenzal chloride of formula (V) were added dropwise at 35° to 40° C. in the course of about 3½ hours. The rate at which the dropwise addition was carried out was so adjusted that the evolution of gas was brisk. After the dropwise addition was complete further stirring was carried out for about ½ an hour, until the evolution of gas was complete. The mixture was poured onto ice, and the product precipitated in the form of crystals. The crystals were taken up in CH₂Cl₂, and the organic layer was separated off and it was washed once with water. It was then dried over Na₂SO₄ and subjected to a column distillation. After the solvent had been distilled off, 2,4-dichloro-5-fluorobenzaldehyde of formula (VII) boiled at a boiling point of 111° and under 20 mbar. The yield was about 75% of theory. The corresponding benzoic acid remained in the residue. The aldehyde of formula (VII) had a melting point of 39° to 41° C.

The 2,4-dichloro-5-fluorobenzaldehyde of formula (VII) was chlorinated at 100° C. under UV irradiation with the theoretical amount of Cl₂. A refractive index of $n_D^{20}$: 1.5748 was obtained thereafter. The system was flushed with nitrogen and the mixture was subjected to a column distillation.

After first runnings of about 2 g, 2,4-dichloro-5-fluorobenzoic acid chloride of formula (I) boiled at boiling point 121°/20 mbar. The refractive index was $n_D^{20}$: 1.5722. The yield was 71% of theory.

On reacting the compound of formula (I) with anhydrous hydrofluoric acid, 2,4-dichloro-5-fluorobenzoyl fluoride of formula (IX), boiling point 98°/15 mbar and $n_D^{20}$: 1.5355 was obtained.

PREPARATION OF STARTING MATERIALS

EXAMPLE 4

(a) 2,4-Dichloro-5-fluorotoluene of formula (III)

528 g of 3-amino-4,6-dichlorotoluene of formula (II) (3 mol), 1.7 liters of water and 600 ml of concentrated HCl were initially introduced into a 4 liter three-necked flask, heated for 1 hour at 50° and cooled down, and a solution of 248 g of sodium nitrite (3.6 mol) in 470 ml of water was added dropwise at 0°. The mixture was further stirred for 30 minutes and thereafter filtered with suction. A diazo solution was obtained.

390 g of an approximately 40% strength dimethylamine solution, 3.2 liters of water, 947 g of sodium carbonate and 1.3 liters of chloroform were initially introduced into a 10 liter three-necked flask. The "diazo solution" was added at −5° to 0° in the course of about 30 minutes, and the mixture was allowed to warm to room temperature and was further stirred for 8 hours at room temperature, whereupon the organic phase was separated off, washed with water, dried and concentrated. Yield: 610 g of crude triazene, melting point 38° to 40° C.

CLEAVAGE 900 ml of anhydrous hydrofluoric acid were initially introduced into a 2 liter stirred autoclave, and 610 g of crude triazine (as a warm melt at approximately 50°) were added at 0° to 10°, whereupon a vigorous exothermic reaction set in. The reaction mixture was then stirred for about 4 hours at 130° to 140° and under 25 bar. Nitrogen was continuously let down via a condenser.

After the reaction was complete the mixture was cooled down and excess hydrofluoric acid was removed in vacuo at room temperature. The residue was worked up wet and distilled. Yield: 365 g of the compound of formula (III) (77.7% of theory), boiling point: 75°/14 mbar, melting point: 23°, $n_D^{20}$: 1.5278.

(b) 2,4-Dichlorofluoro-1-trichloromethylbenzene of formula (IV) and 2,4-dichloro-5-fluorobenzal chloride of formula (V)

2,4-Dichloro-5-fluorotoluene of formula (III) was initially introduced and chlorinated under UV irradiation at a temperature of 110° and 160° C. until the refractive index $n_D^{20}$ was approximately 1.5760. Initially the reaction proceeded exothermally. The quantity of Cl₂ passed in was about 10% above the theoretically calculated quantity.

After the reaction was complete the system was flushed with N₂, and the mixture was fractionated via a column with a silver-coated jacket. About 85% of the desired 2,4-dichloro-5-fluoro-1-trichloromethylbenzene of formula (IV) was obtained as the main fraction at boiling point 145°/15 mbar. The product had a refractive index of $n_D^{20}$: 1.5772.

The first runnings obtained could be re-employed in a subsequent chlorination. However, 2,4-dichloro-5-fluorobenzal chloride of formula (V) could also readily be isolated therefrom at a boiling point of 124°/18 mbar. The refractive index of this product was $n_D^{20}$: 1.5621.

What is claimed is:

1. 2,4-Dichloro-5-fluorobenzoyl chloride of the formula

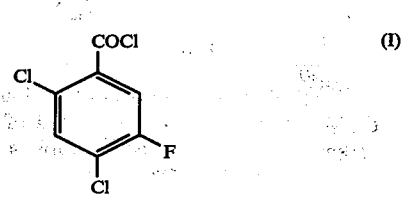

2. A process for the production of 2,4-chloro-5-fluorobenzoyl chloride of claim 1, which comprises reacting (a) 2,4-dichloro-5-fluoro-1-trichloromethylbenzene of the formula

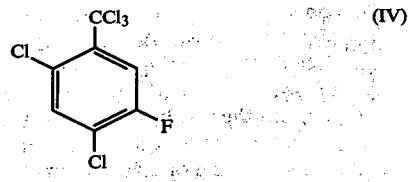

with sulphuric acid to give 2,4-dichloro-5-fluorobenzoic acid of the formula

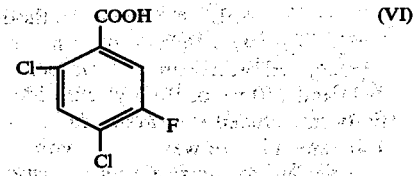

then reacting the resulting 2,4-dichloro-5-fluorobenzoic acid with thionyl chloride to give the compound of formula (I), or (b) reacting 2,4-dichloro-5-fluoro-1-trichloromethyl-benzene of formula (IV) with water in the presence of a catalyst, or (c) reacting 2,4-dichloro-5-fluorobenzal chloride of the formula

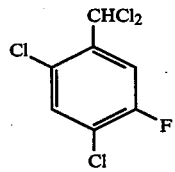
(V)

with sulphuric acid to obtain 2,4-dichloro-5-fluorobenzaldehyde of the formula

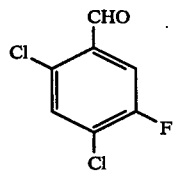
(VII)

then chlorinating to give the compound of formula (I).

3. A process according to claim 2 (a) or 2 (c), in which approximately 95% strength by weight sulphuric acid is used.

4. A process according to claim 2 (b), in which the catalyst is FeCl₃.

5. A process according to claim 2, in which the compound of formula (IV), or the compound of formula (V), has been obtained by diazotising 3-amino-4,6-dichlorotoluene of the formula

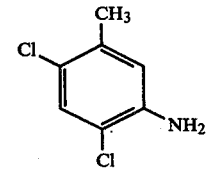
(II)

coupling with dimethylamine, reacting the product with hydrofluoric acid and thermally cleaving the fluorinated product to give 3-fluoro-4,6-dichlorotoluene of the formula

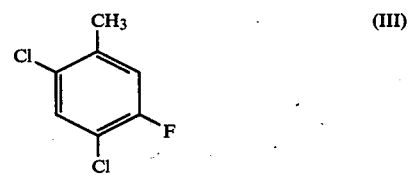
(III)

chlorinating the compound of formula (III), then separating off the desired product of formula (IV) or (V).

6. A process according to claim 5, in which the desired product of formula (IV) or (V) is separated off by distillation.

7. A process according to claim 5 or 6, characterised in that the fluorinated product is subjected to thermal cleavage at a temperature from 130° to 140° C.

8. A process according to claim 5, 6 or 7, in which the compound of formula (III) is chlorinated at a temperature from 110° to 160° C. under UV radiation.

9. 2,4-Dichloro-5-fluorobenzoic acid.

10. A compound according to claim 1 which is 2,4-dichloro-5-fluoro-benzoyl bromide.

11. A compound according to claim 1 which is 2,4-dichloro-5-fluoro-benzoyl fluoride.

12. A compound according to claim 1 which is 2,4-dichloro-5-fluoro-benzoyl chloride.

13. 2,4-Dichloro-5-fluorobenzaldehyde.

14. 2,4-Dichloro-5-fluorobenzal chloride.

15. 2,4-Dichloro-5-fluoro-1-trichloromethylbenzene.

16. 2,4-Dichloro-5-fluorotoluene.

* * * * *